United States Patent [19]

Copp et al.

[11] Patent Number: 4,556,671
[45] Date of Patent: Dec. 3, 1985

[54] PHARMACEUTICAL FORMULATIONS

[75] Inventors: Frederick C. Copp; Kenneth E. Eakins, both of Beckenham, England

[73] Assignee: Burroughs Wellcome Co., Research Triangle Park, N.C.

[21] Appl. No.: 266,477

[22] Filed: May 22, 1981

Related U.S. Application Data

[62] Division of Ser. No. 57,362, Jul. 13, 1979, abandoned.

[51] Int. Cl.$^4$ ............................................. A61K 31/415
[52] U.S. Cl. ..................................................... 514/404
[58] Field of Search .......................... 424/273; 514/404

[56] References Cited

U.S. PATENT DOCUMENTS 3,927,025  12/1975  Korbonits et al. .................. 546/279

OTHER PUBLICATIONS

Chem. Abst., (1971), vol. 74, No. 13146e.

Febs. Letters 110 (2), 213–215, (Feb. 1980), Radmark et al.
Eur. J. Pharmacol. 62, (1980), 121–122, Nijkamp et al.

Primary Examiner—Stanley J. Friedman
Attorney, Agent, or Firm—Donald Brown

[57] ABSTRACT

Heterocyclic compounds of formula (I)

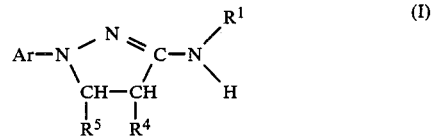

and their acid addition salts, when administered topically, exhibit anti-inflammatory activity and do not produce the side-effects associated with the administration of certain other anti-inflammatories. The compounds of formula (I) may be administered topically as the compound alone or in a suitable topical pharmaceutical formulation.

1 Claim, No Drawings

PHARMACEUTICAL FORMULATIONS

CROSS-REFERENCE TO RELATED APPLICATION

This application is a divisional of our U.S. patent application Ser. No. 057,362, filed on July 13, 1979, now abandoned.

BACKGROUND OF THE INVENTION

This invention relates to topical formulations comprising heterocyclic compounds and their preparation and to their topical use in medicine in a mammal, including man, as anti-inflammatories.

Anti-inflammatory compounds may be assigned to one of two major groups of anti-inflammatory drugs according to their mode of action, namely aspirin-like drugs or corticosteroids. The major disadvantage of the aspirin-like drugs is that they exhibit unfavourable gastro-intestinal side-effects which have been attributed to their selective inhibition of the cyclo-oxygenase pathway of arachidonic acid metabolism (J. R. Vane, Inhibition of prostaglandin synthesis as a mechanism of action for the aspirin-like drugs, Nature (1971) 231, 232). The aspirin-like drugs give good symptomatic relief in chronic inflammation such as analgesia and reduced swelling. However the more chronic, leucocytemediated components of inflammation may proceed unchecked at the low doses administered to avoid the toxic side-effects. The corticosteroid anti-inflammatories do not inhibit oxygenation of arachidonic acid by inhibition of either the cyclo-oxygenase or lipoxygenase pathways in vitro although they have been shown to prevent prostaglandin synthesis in a number of different tissues. The major disadvantage of steroid-like anti-inflammatory drugs is their complicating systemic side-effects.

It is, therefore, an object of the present invention to provide anti-inflammatory formulations which do not exhibit the side-effects associated with these two groups of hitherto-known anti-inflammatory drugs.

U.S. Pat. No. 3,927,025 discloses formulations of compounds of formula (A) and salts thereof which are alleged to have anti-spasmodic activity.

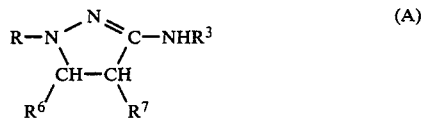

In (A), R is selected from alkyl, cycloalkyl, substituted cycloalkyl, aralkyl, substituted aralkyl, aryl and substituted aryl; $R^6$ and $R^7$ may each be selected from hydrogen, alkyl, substituted alkyl, aryl, substituted aryl; and $R^3$ is selected from hydrogen and the acyl radical of an organic carboxylic acid. Certain of the heterocyclic compounds embraced by formula (A) are known as chemical intermediates in U.S. Pat. No. 4,149,005, and U.K. patent specification Nos. 679678 and 679677. However, none of these patent specifications suggest that any of the compounds of formula (A) possess, or are likely to possess, anti-inflammatory, analgesic or anti-pyretic activity. This is not surprising since none of the antispasmodic agents described in The Pharmacological Basis of Therapeutics, 5th Edition, by Goodman and Gilman, pages 514 to 532 (Macmillian, (1975)) have anti-inflammatory activity and so it would not be expected for an antispasmodic agent to exhibit anti-inflammatory activity. Certain 1-alkyl-3-amino-5-arylpyrazol-2-ines are disclosed in U.K. patent specification No. 1 294 035 as having anti-inflammatory, analgesic or anti-pyretic activity.

SUMMARY OF THE INVENTION

It has now unexpectedly been found that the heterocyclic compounds of formula (I), some of which are members of a class of compounds embraced by formula (A), when administered topically, exhibit a potent anti-inflammatory action in mammals and that such activity can be achieved at doses which do not exhibit the side-effects associated with the administration of the aspirin-like or steroid-like anti-inflammatory drugs.

The heterocyclic compounds referred to herein are of formula (I):

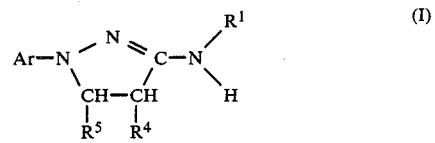

wherein,
  Ar is selected from pyridyl, phenyl and phenyl substituted in one or two positions in the ring by the same or a different substituent, said substituent being selected from trifluoromethyl, fluoro, chloro and bromo;
  $R^1$ is selected from hydrogen and acyl having from 1 to 4 carbon atoms; and
  $R^4$ and $R^5$ are the same or different and each is selected from hydrogen and alkyl having from 1 to 4 carbon atoms;
  and pharmaceutically acceptable acid addition salts thereof.

The anti-inflammatory activity of the heterocyclic compounds of formula (I) on topical administration is unexpected in view of the teaching of the anti-spasmodic activity claimed for them in U.S. Pat. No. 3,927,025. It is even more unexpected since it has been found that the heterocyclic compounds referred to herein have aspirin-like (i.e. peripheral) and not central analgesic activity. In comparison with the compounds disclosed in U.K. patent specification No. 1 294 035, the heterocyclic compounds of formula (I) exhibit more potent anti-inflammatory activity. These heterocyclic compounds inhibit both pathways of arachidonic acid oxygenation i.e. the cyclo-oxygenase and lipoxygenase pathways and this is believed to be responsible for giving these compounds the advantage over aspirin-like drugs of avoiding the possibility of potentiation of lipoxygenase and of having a greater effect in reducing leucocyte migration at doses which inhibit prostaglandin synthesis. The heterocyclic compounds of formula (I) are believed to have a steroid-like profile of anti-inflammatory activity without systemic side-effects normally associated with steroid treatment.

DESCRIPTION OF THE PREFERRED EMBODIMENTS

A sub-class of the heterocylic compounds of formula (I) are those wherein:
  Ar is selected from 2- and 4-pyridyl;
  Ar is selected from 3- and 4-trifluoromethylphenyl;

Ar is phenyl substituted by one or more halogen as defined in the 2-, 3-, 4-, 3,4-, or 2,6-positions;
$R^1$ is hydrogen; and
$R^4$ and $R^5$ are each selected from hydrogen and methyl.

For example:
3-amino-1-(m-trifluoromethylphenyl)-2-pyrazoline;
3-amino-1-(m-trifluoromethyl-p-chlorophenyl)-2-pyrazoline;
3-amino-1-(p-fluorophenyl)-2-pyrazoline;
3-amino-1-(p-fluorophenyl)-4-methyl-2-pyrazoline; and
3-amino-1-(p-fluorophenyl)-5-methyl-2-pyrazoline.

The most preferred compound for topical administration according to the present invention is 3-amino-1-(m-trifluoromethylphenyl)-2-pyrazoline. This compound is equally active in inhibiting cyclo-oxygenase and lipoxygenase activity and does so at doses substantially below those of the other heterocyclic compounds of formula (I).

For topical administration, the acid addition salts of a heterocyclic compounds of formula (I) should be both pharmacologically and pharmaceutically acceptable acid addition salts. Acceptable salts may be derived from organic acids, particularly dicarboxylic acids. Such pharmacologically and pharmaceutically acceptable salts include those prepared from the following acids: hydrochloric, hydrobromic, sulphuric, nitric, phosphoric, oxalic, fumaric, maleic, glycolic, salicylic, succinic, toluene-p-sulphonic, tartaric, acetic, citric, methane-sulphonic, formic, benzoic, malonic, naphthalene-2-sulphonic and benzene-sulphonic.

The heterocyclic compounds of formula (I) may be administered topically to a mammal in need of the inhibition of the cyclo-oxygenase or lipoxygenase pathways of arachidonic acid metabolism. It is known in the art that the inhibition of these pathways could lead to inflammatory activity; thus the compounds of formula (I) may be administered topically in the treatment or prophylaxis of inflammation in a mammal, including man, and may be used in the relief of rheumatoid arthritis, rheumatoid spondylitis, osteoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

The amount of a compound of formula (I) (hereinafter referred to as the active ingredient) required for therapeutic effect on topical administration will, of course, vary with the compound chosen, the nature and severity of the inflammatory condition and the mammal undergoing treatment, and is ultimately at the discretion of the physician. A suitable anti-inflammatory dose of an active ingredient is 0.5 mg to 500 mg of base per kilogram bodyweight for topical administration, the most preferred dosage being 0.5 to 50 mg/kg of mammal bodyweight, for example 5 to 25 mg/kg; administered two or three times daily. For application to the skin, from 1 ug to several mg of active ingredient may be applied per application, preferably from 10 to 100 ug per application.

By topical administration is meant non-systemic administration and includes the application of a heterocyclic compound of formula (I) externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilised by autoclaving or maintaining at 98°–100° C. for half an hour. Alternatively, the solution may be sterilised by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturiser such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicaceous silicas; and other ingredients such as lanolin; may also be included.

According to the present invention there are therefore provided:

(a) heterocyclic compounds of formula (I) and acid addition salts thereof whenever administered topically to a mammal in need thereof;

(b) pharmaceutical formulations suitable for topical administration comprising a non-toxic, effective arachidonic acid oxygenation inhibitory amount of a compound of formula (I) or a pharmaceutically acceptable acid addition salt thereof and a pharmaceutically acceptable carrier therefor;

(c) pharmaceutical formulations suitable for topical administration comprising a non-toxic, effective anti-inflammatory amount of a compound of formula (I) or a pharmaceutically acceptable acid addition salt thereof and a pharmaceutically acceptable carrier therefor;

(d) a method for preparing such formulations;

(e) a method for the prophylaxis or treatment of inflammation in a mammal, including man, comprising the topical administration to said mammal of a non-toxic, effective, anti-inflammatory amount of a compound of formula (I) or a formulation according to (c), supra; and (f) a method for the inhibition of the cyclo-oxygenase and lipoxygenase pathways of arachidonic acid metabolism, comprising the topical administration of an inhibitory amount of a compound of formula (I) or a formulation according to (b), supra.

The following Examples are provided by way of an illustration of the present invention and should in no way be construed as a limitation thereof. All temperatures indicated are in degrees Celsius.

Reference Example 1

Preparation of
3-Amino-1-(m-trifluoromethylphenyl)pyrazol-2-ine

A. Preparation of m-Trifluoromethylphenyl-hydrazine m-Aminobenzotrifluoride (48.34 g: 0.3 mole) was cooled and treated with concentrated hydrochloric acid (137 ml) added dropwise. The paste was stirred at 0° and a solution of sodium nitrite (19.1 g) in water (137 ml) was added at 0°–5° with stirring. An almost clear solution was obtained. Then a solution of stannous chloride dihydrate (191.3 g) in concentrated hydrochloric acid (137 ml) was added dropwise with stirring at 0°–10°.

Then the solid tin complex was filtered off. The solid was then added portionwise to ice-cold 10N-sodium hydroxide (21) and the oil collected into dichloromethane.

The dichloromethane solution was dried over anhydrous sodium sulphate, filtered, evaporated to dryness and distilled in vacuo to yield the title compound (b.p. 83°–108°/0.8 mm Hg.).

B. Preparation of
3-Amino-1-(m-trifluoromethylphenyl)pyrazol-2-ine

Sodium (0.50 g) was dissolved in absolute ethanol (25 ml). m-Trifluoromethylphenyl-hydrazine obtained in Example 1A (17.6 g: 0.1 mole) was then added dropwise with stirring to the clear solution. A pink colour developed. The solution was cooled in ice and acrylonitrile (6.4 ml) added dropwise. The clear pink solution was then stirred under reflux for 6 hours to give a crystalline solid on cooling. The solid was filtered off. On recrystallisation from cyclohexane (ca 400 ml) m.p. of the title compound was 107°–108° (Mettler m.p. 109.1°: started 90° @20°/min) after drying at 0.05 mm/½ hour.

Analysis: $C_{10}H_{10}F_3N$. Found: C, 52.69:H, 4.47: N, 18.27. Required: C, 52.40: H, 4.40: N, 18.33.

EXAMPLES 2–20

In accordance with the method described in Example 1 there were prepared the following:

Reference Example 2

3-Amino-1-p-bromophenyl-2-pyrazoline m.p. 123°–125°.

EXAMPLE 3

3-Amino-1-(3,4-dichlorophenyl)-2-pyrazoline m.p. 184°–185°(efferv.).

Reference Example 4

3-Amino-1-m-chlorophenyl-2-pyrazoline m.p. 129°–130°(decomp.).

Reference Example 5

3-Amino-1-o-chlorophenyl-2-pyrazoline m.p. 104°–105°.

Reference Example 6

3-Amino-1-p-chlorophenyl-2-pyrazoline m.p. 149°–151°.

Reference Example 7

3-Amino-1-phenyl-2-pyrazoline m.p. 164°–166°.

EXAMPLE 8

3-Amino-1-(4-trifluoromethylphenyl)-2-pyrazoline m.p. 150°–151°(decomp.).

EXAMPLE 9

3-Amino-1-(3,5-dichlorophenyl)-2-pyrazoline m.p. 159.5°–160.5°.

EXAMPLE 10

3-Amino-1-(4-chloro-3-trifluoromethylphenyl)-2-pyrazoline m.p. 146°–147°.

Reference Example 11

3-Amino-1-p-fluorophenyl-2-pyrazoline m.p. 114°–115°.

EXAMPLE 12

3-Amino-4-methyl-1-(3-trifluoromethylphenyl)-2-pyrazoline m.p. 73°–74°.

EXAMPLE 13

3-Amino-1-p-fluorophenyl-4-methyl-2-pyrazoline m.p. 121°–123°.

Reference Example 14

3-Amino-5-methyl-1-phenyl-2-pyrazoline m.p. 101°–103°.

EXAMPLE 15

3-Amino-5-ethyl-1-phenyl-2-pyrazoline m.p. 119°–121°.

EXAMPLE 16

3-Amino-1-m-chlorophenyl-4-methyl-2-pyrazoline m.p. 84°–85°.

EXAMPLE 17

3-Amino-1-p-chlorophenyl-5-ethyl-2-pyrazoline m.p. 112°–114°.

EXAMPLE 18

3-Amino-1-p-fluorophenyl-5-methyl-2-pyrazoline m.p. 133°–135°.

Reference Example 19

3-Amino-4-methyl-1-phenyl-2-pyrazoline m.p. 81°–83°.

EXAMPLE 20

3-Amino-1-p-chlorophenyl-4-methyl-2-pyrazoline m.p. 113°–115°.

EXAMPLE 21

Preparation of 3-Amino-1-(m-trifluoromethylphenyl)-2-pyrazoline hydrochloride

3-Amino-1-(m-trifluoromethylphenyl)-2-pyrazoline obtained in Example 1 (4.48 g: 0.02 mole) was dissolved in N-hydrochloric acid (20 ml). The pale orange-coloured solution was then evaporated to dryness in vacuo. The solid residue was dissolved in ethanol containing 5% methanol and re-evaporated to dryness in vacuo, this process was repeated 3 times. The solid was dried at 0.1 mm at room temperature for 30 minutes. Recrystallisation from ethanol containing 5% methanol/ether gave the title compound m.p. 192°–193°.

Analysis: $C_{10}H_{11}F_3ClN_3$. Found: C, 45.04: H, 4.06: N, 15.8. Required: C, 45.21: H, 4.17: N, 15.81.

EXAMPLES 22–24

In accordance with the method described in Example 21 there were prepared the following:

EXAMPLE 22

3-Amino-1-(2,6-dichlorophenyl)-2-pyrazoline hydrochloride monohydrate m.p. 224°–224°(decomp.).

EXAMPLE 23

3-Amino-1-m-chlorophenyl-5-methyl-2-pyrazoline toluene-p-sulphonate m.p. 170°–171°.

EXAMPLE 24

3-Amino-1-p-chlorophenyl-5-methyl-2-pyrazoline hydrochloride m.p. 182°–184°.

EXAMPLE 25

Preparation of 3-Amino-1-(2-pyridyl)-2-pyrazoline

2-Hydrazinopyridine (0.545 g) was added to a solution of sodium (50 mg; 0.43 atoms) in dry absolute ethanol (2 ml) in a nitrogen atmosphere. Acrylonitrile (0.265 g; 0.32 ml; 1 mol) was added dropwise and the resulting solution heated for 4 hours on the steam bath. The reaction mixture was cooled, giving some crystals, and treated with water (10 ml) to give a suspension of a solid. The solid was collected and washed with water. Recrystallisation from ethanol (ca. 5 ml) gave the title compound m.p. 168°–169.5°. Thin Layer Chromatography: On $Al_2O_3$ in $CHCl_3$ gave a single spot Rf 0.18.

EXAMPLE 26

In accordance with the method described in Example 25 there was prepared the following:

EXAMPLE 26

3-amino-1-(4-pyridyl)-2-pyrazoline m.p. 286°–287°(decomp.).

EXAMPLE 27

Preparation of 3-Amino-1-(2-pyridyl)-2-pyrazoline hydrobromide

3-Amino-1-(2-pyridyl)-2-pyrazoline obtained in Example 25 (100 mg) was taken up in ethanol containing 5% methanol (1 ml) and treated with excess concentrated aqueous hydrogen bromide. The resulting suspension of crystals was diluted with diethyl ether (ca. 8 ml) and filtered, and the crystals washed with diethyl ether: 5% methanol in ethanol (50:50). Concentration of the filtrate and treatment with diethyl ether gave more crystals which were discarded.

The pure title compound (99 mg) dissolved in water (1 ml) was treated with excess concentrated aqueous ammonia and set aside to crystallise at 0°; some concentrated aqueous potassium hydroxide was then added and after 10 minutes the pale buff crystals were collected and washed with water m.p. 168°–169.5°.

Reference Example 28

Preparation of 3-Acetylamino-1-(p-chlorophenyl)-2-pyrazoline

3-Amino-1-(p-chlorophenyl)-2-pyrazoline (5 g) was added to acetic anhydride (4.0 ml) at room temperature. On stirring with a glass rod the mixture became warm and afforded a dark red liquid. The mixture was taken up in dichloromethane (100 ml) washed (water, 100 ml; saturated sodium bicarbonate, 100 ml; water, 100 ml), dried over sodium sulphate and the solvent removed in vacuo to afford the title compound (m.p. 171°–173°).

EXAMPLE 29

Preparation of 3-Butyramido-1-(3-chlorophenyl)-2-pyrazoline

In accordance with the method described in Example 28 there was prepared the title compound (m.p. 168°–169°).

Reference Example 30

Preparation of 3-acetamido-4-methyl-1-phenyl-2-pyrazoline

3-Amino-4-methyl-1-phenyl-2-pyrazoline (4.4 g) was added to acetic anhydride (4 ml) at room temperature, and the mixture was stirred for 1 hour. Water was added, the insoluble oil was extracted into chloroform, and the extract was washed with sodium bicarbonate solution and with water, dried (magnesium sulphate) and evaporated to leave a viscous oil. This oil was stirred with methanol to give 3-diacetylamino-4-methyl-1-phenyl-2-pyrazoline which crystallised from methanol as colourless needles.

The methanol filtrate was evaporated to give a second crop of crystals which, after further recrystallisation from benzene/light petroleum (b.p. 60°–80°) and then methanol, gave 3-acetamido-4-methyl-1-phenyl-2-pyrazoline as colourless prisms, m.p. 150°–151°.

EXAMPLES 31 TO 32

In accordance with the method described in Example 28 there were prepared the following:

Reference Example 31

3-Acetamido-5-methyl-1-phenyl-2-pyrazoline m.p. 134°–136°.

EXAMPLE 32

3-Butyramido-5-methyl-1-phenyl-2-pyrazoline m.p. 73°–75°.

Example A: Ointment
Active Ingredient 1.0 g
White Soft paraffin to 100.0 g

Disperse the Active Ingredient in a small volume of the vehicle. Gradually incorporate this into the bulk to produce a smooth, homogeneous product. Fill into collapsible metal tubes.

Example B: Cream for Topical Use
Active Ingredient 1.0 g
Polawax GP 200 20.0 g
Lanolin Anhydrous 2.0 g
White Beeswax 2.5 g
Methyl Hydroxybenzoate 0.1 g
Distilled Water to 100.0 g Heat the Polawax, beeswax and lanolin together at 60°. Add a solution of Methyl Hydroxybenzoate. Homogenise using high speed stirring. Allow temperature to fall to 50°. Add and disperse the active ingredient. Allow to cool with slow speed stirring.

Example C: Lotion for Topical Use
Active Ingredient 1.0 g
Sorbitan Monolaurate 0.6 g
Polysorbate 20 0.6 g
Cetostearyl Alcohol 1.2 g
Glycerin 6.0 g
Methyl Hydroxybenzoate 0.2 g
Purified Water B.P. to 100.00 ml The Methyl Hydroxybenzoate and Glycerin were dissolved in 70 ml of the water at 75°. The Sorbitan Monolaurate, Polysorbate 20 and Cetostearyl Alcohol were melted together at 75° and added to the aqueous solution. The resulting emulsion was homogenised, allowed to cool with continuous stirring and the Active Ingredient added as a suspension in the remaining Water. The whole was stirred until homogenised.

Example D: Eye Drops
Compound of Example 21 0.5 g
Methyl Hydroxybenzoate 0.01 g
Propyl Hydroxybenzoate 0.04 g
Purified Water B.P. to 100.00 ml The Methyl and Propyl Hydroxybenzoates were dissolved in 70 ml Purified Water at 75° and the resulting solution then allowed to cool. The compound of Example 21 was then added and the solution made up to 100 ml with purified water. The solution was sterilised by filtration through a membrane filter 0.22 μm pore size and packed aseptically into suitable sterile containers.

Example I

Acute Anti-inflammatory Activity: Carrageenin Test

Female Wistar rats (100–150 g, groups of 5) were starved for approximately 24 hours prior to testing and througout the experimental period. Water was available ad. lib. Drugs were administered orally, by stomach tube, as a suspension of 0.25% Celacol in water, in a volume of 1 ml per 100 g bodyweight. A control group received Celacol alone. Immediately after dosing, each rat received, in a plantar area of the left hind foot, an injection of 0.1 ml of the supernatant of a 30 mg/ml suspension of carrageenin in 0.9% saline. The thickness of the foot was measured with calipers 1 hour and 4 hours after the carrageenin injection. The increases in foot thickness during this time was compared with those of the control group and the percentage reduction in swelling calculated for each tested group. The results are shown in Table 1.

TABLE 1

| Active Ingredient | $ED_{50}$ |
|---|---|
| 3-Amino-1-(m-trifluoromethylphenyl)-2-pyrazoline | 11 |
| 3-Amino-1-p-chlorophenyl-2-pyrazoline | 22 |
| 3-Amino-1-phenyl-2-pyrazoline | 60 |
| 3-Amino-5-methyl-p-chlorophenyl-2-pyrazoline hydrochloride | 36 |
| Phenylbutazone | 22 |
| Aspirin | 70 |

Example II

Inhibition of Lipoxygenase and Cyclo-oxygenase

In an enzyme assay according to the method of G. J. Blackwell and R. J. Flower (Br. J. Pharmac., 63, 360P, (1978)), the compound of Example 1 was tested over a wide range of concentrations. 3-Amino-1-(m-trifluoromethylphenyl)-2-pyrazoline gave a concentration-dependent inhibiton of lipoxygenase ($IC_{50}=0.72$ μg/ml) and cyclo-oxygenase ($IC_{50}=2.80$ μg/ml) and reduced the production of HETE by less than 20% at 100 μg/ml.

Example III

Induction and Collection of Inflammatory Exudates

Inflammatory exudates were induced and collected by the subcutaneous implantation of polyester sponges impregnated with carrageenin (20 mg/ml sterile saline) in male rats (200 g) (Higgs et al: Advances in Prostaglandin and Thromboxane Research, Vol. 1 p. 105 (1976)).

The sponges were removed after 24 hours, immersed in 5 ml herparinised saline and squeezed until dry. Total leukocyte numbers in sponge exudates were estimated using "Improved Neubauer" counting chambers and Phase Contrast Microscopy Results are given in Table 3.

TABLE 3

| Results of Example III Assay | | |
|---|---|---|
| Active Ingredient | Inhibition of Leukocyte Migration | Reduction of Prostaglandin Concentration |
| Indomethacin (4 mg/kg) p.o. | 26% ± 7 s.e.m | 98% |
| 3-amino-1-m-trifluoromethylphenylpyrazol-2-ine (50 mg/kg) p.o. | 73% ± 9 s.e.m | 69% ± s.e.m |
| Dexamethasone (0.1 mg/kg) p.o. | ~30% | ~30% |
| Dexamethasone (0.1 mg/kg) i.m. | 62% ± 17 s.e.m | 64% ± 6 s.e.m |

Example IV

PBQ-Induced Algesia

An irritant, p-phenylbenzquinone (PBQ), was administered to mice intraperitoneally at a dose of 5 mg/kg to elicit a stretch-reflex in the animal. The number of stretches in 25 minute period were counted.

The same test (Siegmund, E., Cadmus, R, and Lu, G: Proc. Soc. Exp. Biol. Med. 95, 729, (1957)) was performed after orally administering an active ingredient 30 mins prior to the injection of PBQ. The dose of the active ingredient required to reduce the number of stretches by 50% was recorded and are shown in Table 4.

TABLE 4

Results of PBQ-Induced Algesia Assay

| Active Ingredient | $ED_{50}$ (mg/kg) p.o. |
|---|---|
| 3-Amino-1-p-chlorophenyl-2-pyrazoline | 13 |
| 3-Amino-1-m-trifluoromethylphenyl-2-pyrazoline | 20.6 |
| Aspirin | 70 |

We claim:

1. The method of inhibiting cyclo-oxygenase and lipoxygenase enzymes in a mammal in need thereof which comprises the topical administration to said mammal of inhibitory amount of 3-amino-1-(m-trifluoromethyl-phenyl)-2-pyrazol-2ine or a pharmaceutically acceptable acid addition salt thereof to inhibit said enzymes.

* * * * *